June 27, 1961 J. GERLING Plant Pat. 2,065
ORNAMENTAL CHERRY TREE
Filed March 22, 1960
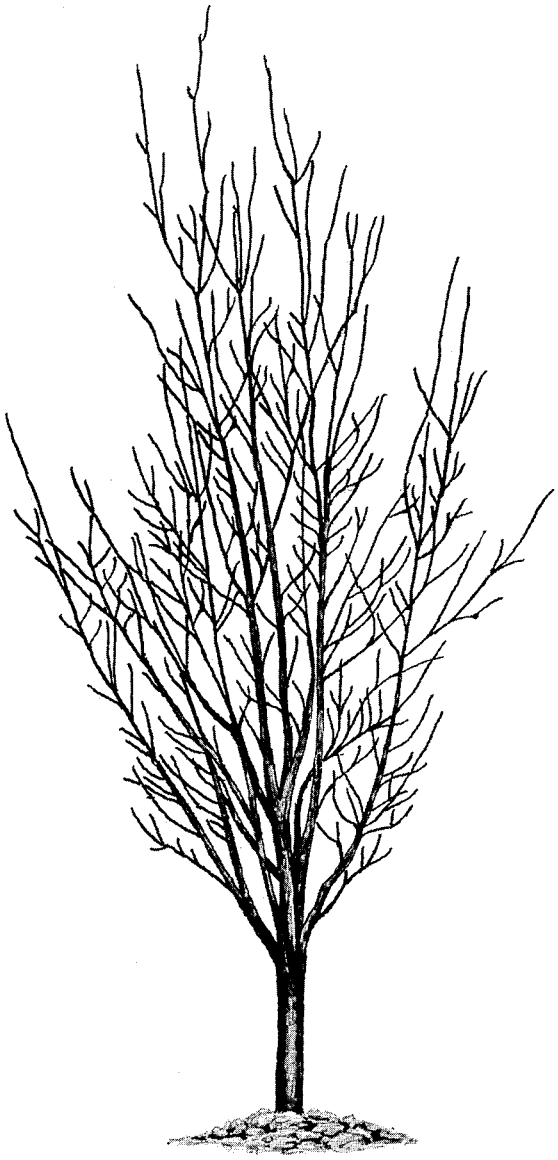
INVENTOR
JACOB GERLING
By: Williams, Tilberry & Golrick
ATTORNEYS United States Patent Office Plant Pat. 2,065
Patented June 27, 1961

2,065
ORNAMENTAL CHERRY TREE

Jacob Gerling, Rochester, N.Y., assignor to
Edward H. Scanlon, Olmsted Falls, Ohio
Filed Mar. 22, 1960, Ser. No. 16,896
1 Claim. (Cl. 47—60)

The present invention or discovery relates to a new and distinct variety of cherry tree of the species *Prunus sargenti.*

This new variety of cherry tree maintains the rose color of the flowers and the brilliant red of the fall foliage which are characteristic of the species; but in contrast with the species has a true columnar form. The new variety of cherry tree thus has decidedly desirable features for landscape, street, and ornamental planting by virtue of the retained colorful characteristics of the species, while having a pleasing columnar form which decreases the planting area that must be appropriated to the individual tree.

The drawing represents the tree in the dormant state to show more clearly the manner and direction of branching giving rise to the columnar form.

This new variety of cherry tree has a true and distinctly columnar form with major branches leaving the trunk and smaller branches leaving the major branches either in a sharply ascending direction or in disposition even approaching right angles but then turning sharply to ascend in a direction approaching parallelism to the trunk, resulting in a spread not exceeding more than about ten feet in a mature tree. It is by the form only that the new variety of cherry tree is distinguished from the species.

In contrast for example with another variety of the species *Prunus sargenti,* namely the variety *Prunus sargenti pyramidalis* which is rather cone-shaped having a broad base upwardly convergent to a narrow top, the instant variety tends to maintain its width from the base upward.

The parent tree was selected, because of the upright growth habit definitely shown in this individual seedling when three feet tall, from among several naturally sown seedlings growing near a roadside planting of mature cherry trees of the species *Prunus sargenti,* all having the full, rounded heads typical of the species. Selection was made in the summer of 1946, along Pinegrove Road in Irandequoit, New York. The selected seedling was transplanted in the fall of 1946 to a location where it could be closely observed while developing: such observation being essential in determining whether or not the upright branch structure, so marked in the young plant, was a dominant character which would prove persistent in future growth. Upright branching habit retained after 14 years was considered conclusive proof.

Asexual propagation of more than a thousand propagules through budding—both directly from the parent and from other propagules—at Olmsted Falls, Ohio, has confirmed the columnar habit in the clone and established this as a distinct variety.

I claim:

A new and distinct variety of cherry tree of the species *Prunus sargenti,* substantially as herein shown and described, characterized particularly as to novelty by its distinctly columnar form, and otherwise retaining the characteristics of the species.

No references cited.